US006383527B1

(12) United States Patent
Artman et al.

(10) Patent No.: US 6,383,527 B1
(45) Date of Patent: May 7, 2002

(54) COMPOSITIONS COMPRISING VALERIAN EXTRACTS, ISOVALERIC ACID OR DERIVATIVES THEREOF WITH A NSAID

(75) Inventors: Linda D. Artman, Salt Lake City; Manuel F. Balandrin, Sandy, both of UT (US)

(73) Assignee: NPS Pharmaceuticals, Inc., Salt Lake City, UT (US)

( * ) Notice: Subject to any disclaimer, the term of this patent is extended or adjusted under 35 U.S.C. 154(b) by 0 days.

(21) Appl. No.: 09/623,384

(22) PCT Filed: Mar. 4, 1999

(86) PCT No.: PCT/US99/04786

§ 371 Date: Sep. 1, 2000

§ 102(e) Date: Sep. 1, 2000

(87) PCT Pub. No.: WO99/44623

PCT Pub. Date: Sep. 10, 1999

(51) Int. Cl.[7] .............................................. A01N 65/00
(52) U.S. Cl. ........................ 424/733; 514/576; 514/577; 514/162
(58) Field of Search .......................... 424/733; 514/576, 514/577, 162

(56) References Cited

U.S. PATENT DOCUMENTS 3,485,851 A * 12/1969 Thies ...................... 260/345.2

FOREIGN PATENT DOCUMENTS

| DE | 2230626 | * | 1/1994 | .......... A61K/27/14 |
| WO | 94-28888 | * | 12/1994 | .......... A61K/31/16 |
| WO | 98-08498 | * | 3/1998 | .......... A61K/31/16 |

OTHER PUBLICATIONS

BNSDOCID, "Monographs on Drugs and Ancillary Substances" (1993).*
Morazzoni et al. Fitoterapia, vol. LXVI, 190 2, pp.–112 (1995).*
Hazelhoff et al, Arch. Int. Pharma., vol. 257, pp. 274–87 (1982).*

* cited by examiner

Primary Examiner—James H. Reamer
(74) Attorney, Agent, or Firm—Foley & Lardner (57) ABSTRACT

Preparations and extracts of valerian, as well as isovaleramide, isovaleric acid, and its pharmaceutically acceptable salts, esters, and substituted amides, and other valerian-related compounds, in combination with NSAIDs exhibit clinically significant pharmacological properties which implicate a treatment for acute muscular aches, strains, and sprains which occur from a localized, external insult to a particular muscle or muscle group outside of, or peripheral to, the CNS. The compositions in question generally are non-cytotoxic and do not elicit weakness or sedative activity at doses that are effective for the symptomatic treatment of such pathological conditions.

39 Claims, 2 Drawing Sheets

FIG. 1

2-methyl isovaleramide 3-methyl isovaleramide 2,2-dimethyl isovaleramide 2,3-dimethyl isovaleramide 4-methyl isovaleramide 2,4-dimethyl isovaleramide 3,4-dimethyl isovaleramide 2,2,4-trimethyl isovaleramide 3-hydroxy isovaleramide 4-hydroxy isovaleramide 4-hydroxy-3-methyl isovaleramide N-(2-acetamido) isovaleramide 2-hydroxyl isovaleramide 2-methyl-1-propyl sulfonamide 1-methylethyl sulfamate 2-methyl-1-propyl sulfamate Isopropyl carbamate Isobutyl carbamate

FIG. 2

COMPOSITIONS COMPRISING VALERIAN EXTRACTS, ISOVALERIC ACID OR DERIVATIVES THEREOF WITH A NSAID

BACKGROUND OF THE INVENTION

The present invention relates to the novel combination therapy of valerian-related products and valerian extracts in combination together with anti-inflammatory agents such as the non-steroidal anti-inflammatory drugs (NSAIDs) to elicit greater, improved relief from pain and muscle tension due to stress or injury. More particularly, the invention provides therapeutic combinations of isovaleramide, isovaleric acid, and/or related compounds with NSAIDs, such as ibuprofen, and methods for using these combinations for treating patients suffering from acute lower back pain.

Many agents currently employed in the treatment of muscle pain, such as lower back pain, reduce inflammation, yet provide no decrease in muscle tone, which is a significant component of acute muscle pain. Likewise, many of the currently employed agents that elicit a decrease in muscle tone, for example, benzodiazepines, do not reduce inflammation.

It is apparent, therefore, that compositions that can both reduce inflammation and elicit a decrease in muscle tone are greatly to be desired. It also is apparent that improved methods for treating pain and muscle tension are highly desirable.

SUMMARY OF THE INVENTION

Accordingly, it is an object of the present invention to provide a therapeutic combination of valerian extract and/or valerian-related compounds together with at least one NSAID for the improved relief from pain and muscle tension due to stress or injury.

It also is an object of the present invention to provide a method for alleviating one or more symptoms associated with acute muscle pain that is ameliorated by means of a decrease in muscle tone.

It is another object of the present invention to provide a novel combination therapy for the treatment of treating a pathology that is ameliorated by a decrease in muscle tone and a reduction in inflammation.

In accomplishing these and other objectives, there has been provided, according to one aspect of the present invention, the use of a combination of: (a) at least one non-steroidal anti-inflammatory compound, and; (b) at least one compound selected from the group consisting of isovaleric acid, a pharmaceutically acceptable salt of isovaleric acid, a pharmaceutically acceptable ester of isovaleric acid, a pharmaceutically acceptable amide of isovaleric acid and a compound having the structure:

where A=H, CH$_3$ or OH,
B=H, OH, or CH$_3$,
X=CH$_2$, CHCH$_3$, C(CH$_3$)$_2$, —O—, CH(OH)—, or —CH$_2$O—,
Y=—CO—, or —SO$_2$—, and
Z=H, CH$_2$CO$_2$H, or CH$_2$CONH$_2$ and where the compound is selected from the group consisting of 2-methyl isovaleramide, 3-methylisovaleramide, 2,2-dimethylisovaleramide, 2,3-dimethylisovaleramide, 4-methylisovaleramide, 2,4-dimethylisovaleramide, 3,4-dimethylisovaleramide, 2,2,4-trimethylisovaleramide, 3-hydroxyisovaleramide, 4-hydroxyisovaleramide, 4-hydroxy-3-methyl-isovaleramide, 2-hydroxyisovaleramide, N-(2-acetamido) isovaleramide, 2-methyl-1-propyl sulfonamide, 1-methylethyl sulfamate, 2-methyl-1-propyl sulfamate, isopropyl carbamate, and isobutylcarbamate, in the preparation of a pharmaceutical formulation for use in a method of treating a pathology that is ameliorated by a decrease in muscle tone and a reduction in inflammation, whereby at least one symptom of that pathology is alleviated.

In accordance with another aspect of the invention, the pathology is selected from the group consisting of acute muscular aches, strains, and sprains which occur from a localized, external insult to a particular muscle or muscle group outside of, or peripheral to, the CNS. In one embodiment, the pathology is lower back pain, and in another embodiment, the pathology is ameliorated by a decrease in inflammation, pain, and muscle tone.

In accordance with yet another aspect of the invention, the non-steroidal anti-inflammatory compound is selected from the group consisting of aspirin, a non-steroidal anti-inflammatory acetic acid, a fenamate, an oxicam, and a non-steroidal anti-inflammatory propionic acid. In one embodiment, the non-steroidal anti-inflammatory compound is selected from the group consisting of sodium salicylate, acetaminophen, phenacetin, ibuprofen, ketoprofen, indomethacin, flurbiprofen, diclofenac, naproxen, piroxicam, tebufelone, etodolac, nabumetone, tenidap, alcofenac, antipyrine, amimopyrine, dipyrone, animopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, meclofenamic acid, mefenamic acid, niflumic acid, salidifamides, sulindac, suprofen, tolmetin, nabumetone, tiaramide, proquazone, bufexamac, flumizole, tinoridine, timegadine, dapsone, diflunisal, benorylate, fosfosal, fenclofenac, etodolac, fentiazac, tilomisole, carprofen, fenbufen, oxaprozin, tiaprofenic acid, pirprofen, feprazone, piroxicam, sudoxicam, isoxicam, celecoxib, Vioxx® and tenoxicam. In another embodiment, the non-steroidal anti-inflammatory compound is selected from the group consisting of aspirin, sodium salicylate, acetaminophen, ibuprofen, ketoprofen, and naproxen.

In accordance with still another aspect of the invention, the composition comprises a pharmaceutically acceptable amide of isovaleric acid, where the amide is isovaleramide. In preferred embodiments, the composition comprises isovaleramide together with ibuprofen, aspirin, acetaminophen, acetylsalicylic acid, naproxen, or ketoprofen.

In accordance with a still further aspect of the invention there has been provided a use of an extract of Valerianaceae, cramp bark, black haw, or hops in combination with at least one non-steroidal anti-inflarnmatory compound in the preparation of a pharmaceutical formulation for use in a method of treating acute muscular aches, strains, and sprains which occur from a localized, external insult to a particular muscle or muscle group outside of, or peripheral to, the CNS wherein the extract comprises at least one compound that is hydrolyzed in vivo to yield isovaleric acid or isovaleramide. In particular embodiments the non-steroidal anti-inflammatory compound is ibuprofen, aspirin, acetaminophen, acetylsalicylic acid, naproxen, or ketoprofen.

In accordance with yet another aspect of the invention there has been provided a pharmaceutical composition comprising (a) at least one non-steroidal anti-inflammatory compound, and; (b) at least one compound selected from the group consisting of isovaleric acid, a pharmaceutically acceptable salt of isovaleric acid, a pharmaceutically acceptable ester of isovaleric acid, a pharmaceutically acceptable amide of isovaleric acid and a compound having the structure:

where A=H, CH$_3$ or OH,
  B=H, OH, or CH$_3$,
  X=CH$_2$, CHCH$_3$, C(CH$_3$)$_2$, —O—, CH(OH)—, or —CH$_2$O—,
  Y=—CO—, or —SO$_2$—, and
  Z=H, CH$_2$CO$_2$H, or CH$_2$CONH$_2$
and where that compound is selected from the group consisting of 2-methyl isovaleramide, 3-methylisovaleramide, 2,2-dimethylisovaleramide, 2,3-dimethylisovaleramide, 4methylisovaleramide, 2,4-dimethylisovaleramide, 3,4-dimethylisovaleramide, 2,2,4-trimethylisovaleramide, 3-hydroxyisovaleramide, 4-hydroxyisovaleramide, 4-hydroxy-3-methyl-isovaleramide, 2-hydroxyisovaleramide, N-(2-acetamido)isovaleramide, 2-methyl-1-propyl sulfonamide, 1-methylethyl sulfamate, 2-methyl-1-propyl sulfamate, isopropyl carbamate, and isobutylcarbamate, together with a pharmaceutically acceptable diluent, excipient, or carrier.

In one embodiment, the non-steroidal anti-inflammatory compound is selected from the group consisting of aspirin, a non-steroidal antiinflammatory acetic acid, a fenamate, an oxicam, and a non-steroidal anti-inflammatory propionic acid. In another embodiment, the non-steroidal anti-inflammatory compound is selected from the group consisting of sodium salicylate, acetaminophen, phenacetin, ibuprofen, ketoprofen, indomethacin, flurbiprofen, diclofenac, naproxen, piroxicam, tebufelone, etodolac, nabumetone, tenidap, alcofenac, antipyrine, amimopyrine, dipyrone, animopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, meclofenamic acid, mefenamic acid, niflumic acid, salidifamides, sulindac, suprofen, tolmetin, nabumetone, tiaramide, proquazone, bufexamac, flumizole, tinoridine, timegadine, dapsone, diflunisal, benorylate, fosfosal, fenclofenac, etodolac, fentiazac, tilomisole, carprofen, fenbufen, oxaprozin, tiaprofenic acid, pirprofen, feprazone, piroxicam, sudoxican, isoxicam, celecoxib, Vioxx® and tenoxicam. In yet another embodiment, the non-steroidal anti-inflammatory compound is selected from the group consisting of aspirin, sodium salicylate, acetaminophen, ibuprofen, ketoprofen, and naproxen.

In a particular embodiment, the composition comprises a pharmaceutically acceptable amide of isovaleric acid, where that amide is isovaleramide. In other embodiments, the composition comprises isovaleramide together with aspirin, sodium salicylate, acetaminophen, ibuprofen, ketoprofen, or naproxen.

In accordance with a still further aspect of the invention, there has been provided a pharmaceutical composition comprising an extract of Valerianaceae, cramp bark, black haw, or hops and at least one non-steroidal anti-inflammatory compound, together with a pharmaceutically acceptable diluent, excipient, or carrier. In particular embodiments the non-steroidal anti-inflammatory compound is aspirin, sodium salicylate, acetaminophen, ibuprofen, ketoprofen, or naproxen.

Other objects, features, and advantages of the present invention will become apparent from the following detailed description. It should be understood, however, that the detailed description and the specific examples, while indicating preferred embodiments of the present invention, are given by way of illustration only, since various changes and modifications within the spirit and scope of the invention will become apparent to those skilled in the art from this detailed description.

DETAILED DESCRIPTION OF THE PREFERRED EMBODIMENTS

Valerian extracts and valerian-related compounds can be administered in combination with at least one NSAID compound, such as ibuprofen, in vivo to reduce acute muscle pain by decreasing muscle tone and inflammation. That is, this combination therapy surprisingly provides greatly improved relief of muscle inflammation and tone as compared to administration of either NSAIDs or valerian-related compounds and extracts alone.

The valerian extracts that are suitable for use in the invention are those extracts that, upon hydrolytic or metabolic breakdown in vivo, release isovaleric acid, isovaleramide, or a related compound. These extracts may be used in combination with at least one NSAID. The extracts may be coadministered with the NSAID(s), or may be formulated into a pharmaceutical composition with the NSAID(s) so that the extract and the NSAID(s) are delivered to the patient essentially simultaneously. The skilled artisan also will recognize that the present invention also comprehends the use of compositions containing (i): (a) combinations of valerian extracts with valerian-related compounds such as isovaleramide, together with (b) one or more NSAID compounds; and (ii) (a) a single valerian extract or valerian-related compound, together with (b) one or more NSAID compounds.

Figure 1:
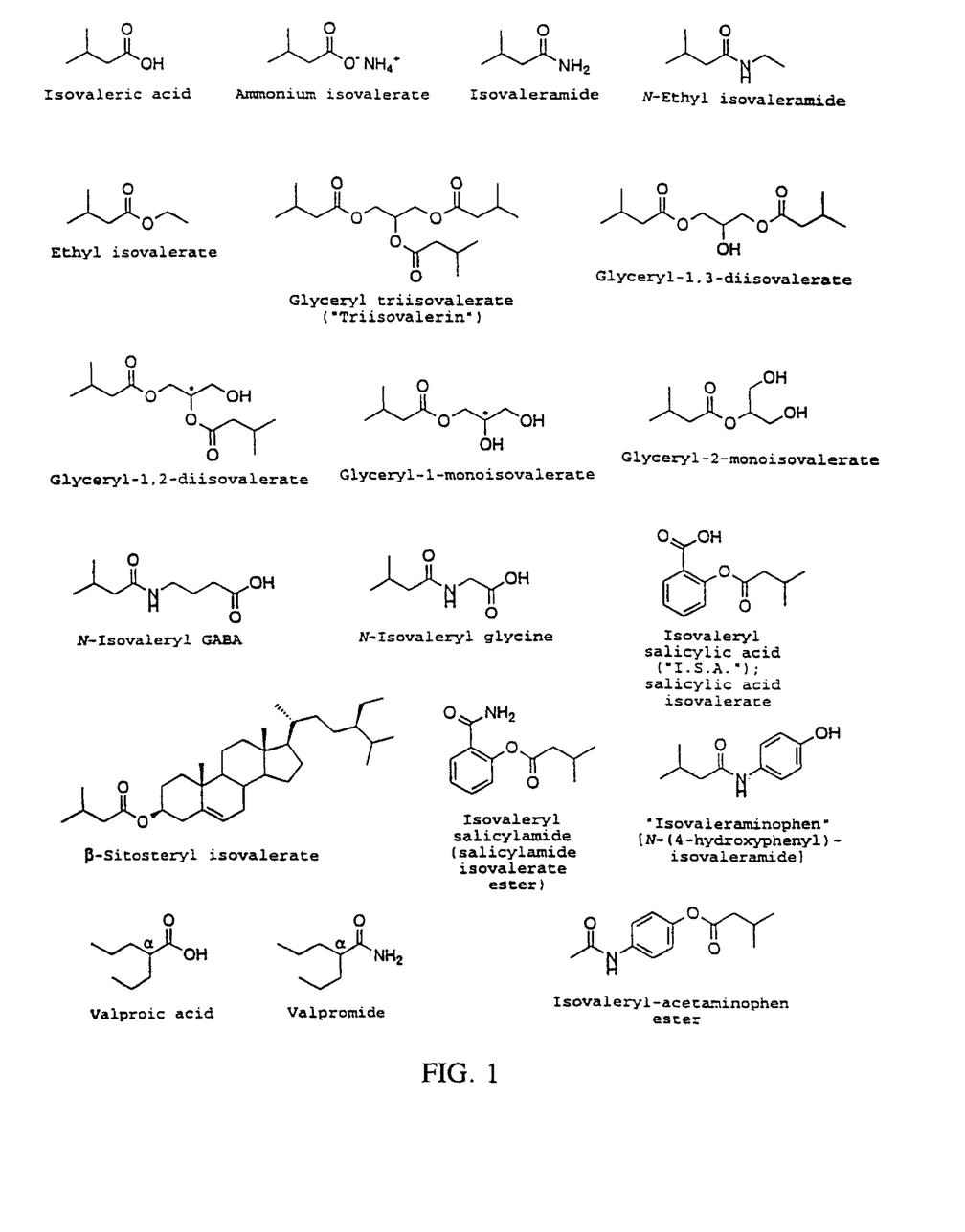
FIG. 1 depicts the structures of isovaleramide and various structurally-related compounds, including isovaleramide.
Figure 2:
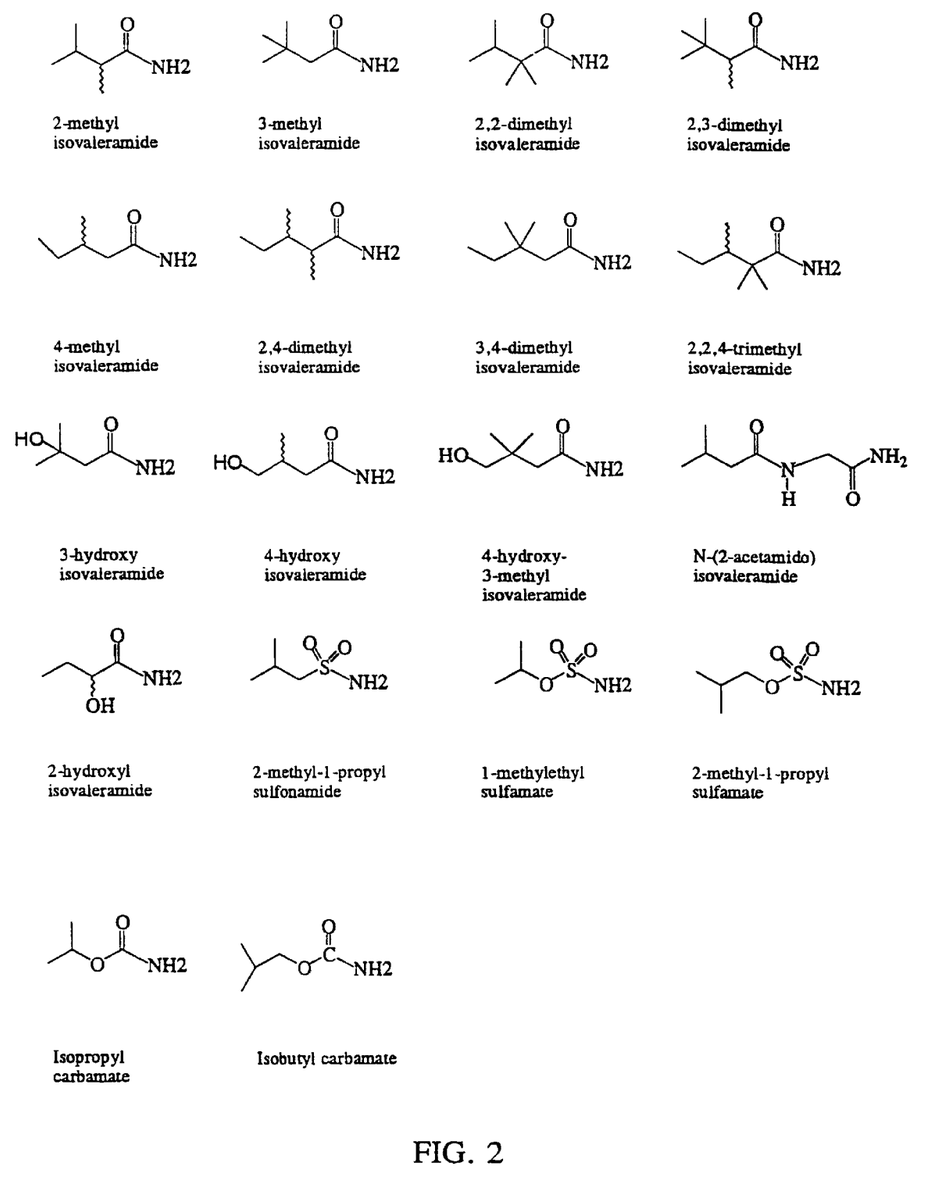
FIG. 2 depicts the structures of additional compounds that are structurally related to isovaleramide.

In the context of the present invention, a valerian-related compound is a compound selected from the group consisting of isovaleric acid, a pharmaceutically acceptable salt of isovaleric acid, a pharmaceutically acceptable ester of isovaleric acid, isovaleramide, or another pharmaceutically acceptable amide of isovaleric acid, and a compound having the structure where A=H, CH$_3$ or OH,
B=H, OH, or CH$_3$,
X=CH$_2$, CHCH$_3$, C(CH$_3$)$_2$, —O—, CH(OH)—, or —CH$_2$O—,
Y=—CO—, or —SO$_2$—, and
Z=H, CH$_2$CO$_2$H, or CH$_2$CONH$_2$ The structures of these compounds are shown in FIGS. 1 and 2 and include substituted isovaleramides such as 2-methylisovaleramide, 3-methylisovaleramide, 2,2-dimethylisovaleramide, 2,3-dimethylisovaleramide, 4-methylsovaleramide, 2,4-dimethylisovaleramide, 3,4-dimethylisovaleramide, 2,2,4-trimethylisovaleramide, 3-hydroxyisovaleramide, 4-hydroxyisovaleramide, 4-hydroxy-3-methylisovaleramide, 2-hydroxyisovaleramide, and 2,2-dimethyl-n-butyramide. The valerian-related compounds also include certain sulfonamide, sulfamate, and carbamate compounds that, by virtue of their structural similarity to isovaleramide, share similar pharmacological activities. Preferred sulfonamides and sulfamates include 2-methyl-1-propylsulfonamide, 1-methylethyl sulfamate, and 2-methyl-1-propyl sulfamate. Preferred carbamates include isobutylcarbamate (CH$_3$)$_2$CHCH$_2$OCONH$_2$) and isopropylcarbamate (CH$_3$)$_2$CHOCONH$_2$).

For each of these compounds that contains one or more asymmetric centers, the present invention specifically includes each of the possible enantiomeric or diastereomeric forms of the compound. The nature of the valerian-related compounds and the NSAID compounds are discussed in more detail below.

In the context of the present invention, compounds are said to be "coadministered" to a patient when the compounds are administered at times that are sufficiently close together that the compounds are pharmacologically active and present in a pharmaceutically effective concentration in the patient at the same time. For example, a valerian extract may be administered to a patient some time after administration of an NSAID, but is considered to be coadministered with the NSAID if the NSAID is still present in a pharmaceutically effective concentration in the patient.

Methods For Preparing Pharmaceutical Formulations

Preparation of Active Compounds

The rhizomes and roots of Valeriana spp. (common name: valerian; family Valerianaceae) have been used for medicinal purposes since ancient times. The most commonly used valerian preparations include aqueous and hydroalcoholic extracts, such as tinctures, intended for oral administration. In addition, ammoniated valerian tinctures were used medicinally in the English-speaking world since at least the beginning of the seventeenth century. Hobbs, HerbalGram No. 21: 19–34 (1989). In the last three decades, the sedative and antispasmodic properties of valerian preparations have been attributed primarily to the presence of chemically labile monoterpenoid iridoid triester compounds called valepotriates ("valerian-epoxy-triesters (-ates)").

The most common and abundant of the valepotriates, valtrate and didrovaltrate, each contain two isovalerate moieties esterified to a "central" iridoid nucleus. Lin et al., Pharm. Res. 8: 1094–1102 (1991). However, these acid- and heat-labile substances do not survive intact in the stomach following oral administration, and readily release two moles of isovaleric acid for every mole of valepotriate. Furthermore, aqueous extracts of valerian rhizomes and roots retain their biological properties, even though the valepotriate triesters are water-insoluble. Bos et al., Phytochem. Anal. 7: 143–51 (1996).

The major, water-soluble, active principle of commonly used valerian extracts and other preparations, such as aqueous or hydroalcoholic extracts or tinctures, has been determined to be the ester hydrolysis product, isovaleric acid. Ammonium isovalerate and isovaleramide are produced in ammoniated tinctures. Balandrin et al., J. Toxicol.-Toxin Rev. 14: 165 (1995). The structures of isovaleramide and structurally-related compounds are depicted in FIGS. 1 and 2. In this way, the chemically labile valepotriates and other valerian-derived monoterpenoid-isovalerate esters, such as bornyl and lavandulyl isovalerates, act as "pro-drugs" and chemical precursors for isovaleric acid, its salts, and isovaleramide.

Isovaleramide has been isolated from valerian plants, most probably as an isolation artifact following treatment with ammonia. Buckova et al., Cesk. Farm. 26: 308 (1977); Chem. Abstr. 88: 86063z (1978); see also Bos et al. and Fuzzati et al., Phytochem. Anal. 7: 143, 76 (1996). More recently, isovaleramide was shown to exhibit low acute toxicity in vivo, no mutagenic potential, and clinically useful anxiolytic properties. U.S. Pat. No. 5,506,268; PCT application WO 94/28,888. Methods for preparing isovaleramide are well known.

Extracts of medicinal plants that are useful for treating the symptoms of muscle (or muscular) tension can be prepared by aqueous, hydroalcoholic, or alcoholic extraction, or by extraction with other suitable solvents using methods well known to those of skill in the art. In the context of the present invention, useful extracts contain at least one of the following: isovaleric acid, its salts or complexes, ethyl isovalerate, isovaleramide, N-ethyl isovaleramide, and their chemical precursors. Useful extracts also share the common property of releasing isovaleric acid and/or isovaleramide upon hydrolysis in vivo. Standard methods for preparing such extracts can be found in pre-1950 editions of the U.S. PHARMACOPOEIA (U.S.P.) and the NATIONAL FORMULARY (N.F.), as well as in well-known references such as Gennaro (Ed.), REMINGTON'S PHARMACEUTICAL SCIENCES, 18th ed. (Mack Publishing Co. 1990), Tyler et al., PHARMACOGNOSY, 9th ed. (Lea and Febiger 1988), and Hare et al., THE NATIONAL STANDARD DISPENSATORY (Lea Brothers 1905). Additional citations appear in U.S. Pat. No. 5,506,268 and PCT application WO 94/28,888, which are hereby incorporated by reference in their entirety.

The principal historic sources of naturally occurring isovaleric acid have been valerian rhizomes and roots, as well as those of closely related plants in the family Valerianaceae. As discussed by Hobbs (1989), supra, these include the common valerian plant, Valeriana officinalis L., as well as the East Indian valerian, V. wallichii DC., and the biblical spikenard, Nardostachys jatamansi (Roxb.) DC. In addition to valerian rhizomes and roots, other plants which have been used traditionally as sedative or "antispasmodic" herbal medicines are known to contain, or to produce, isovaleric acid. These include hops (Humulus lupulus L., family Moraceae, which is often used in herbal formulations in combination with valerian), "cramp bark" or "guelder rose" (Viburnum opulus L., family Caprifoliaceae), and "black haw" (V. prunifolium L., root bark). Hare et al., THE NATIONAL STANDARD DISPENSATORY, pages 93, 94, 159, 160, 169, 256, 642, 692–694, 766, 767, 932, 1031, 1383, 1384, 1426, 1479, 1480, 1571, 1572, 1619, 1620, 1631–1633, 1661, and 1662 (Lea Brothers 1905); Heyl et al., *J. Am. Chem. Soc.* 42: 1744 (1920); Grier, *Pharm. J. Pharm.* 68: 302 (1929); Grier, *Chem. Drug. (London)* 110: 420 (1929); Grieve, A MODERN HERBAL, pages 35–40, 265–276, 381, 382, 411–415, 744–746, 781, 782, and 824–830 (Hafner 1959); Holbert, *J. Am. Pharm. Assoc., Sci. Ed.* 35: 315 (1946); Hoffmann, THE HERBAL HANDBOOK: A USER'S GUIDE TO MEDICAL HERBALISM, pages 38, 39, 83 and 84 (Healing Arts Press 1989).

As in the case of valerian rhizomes and roots, hops generate isovaleric acid from more chemically complex precursors upon oxidation or enzymatic breakdown. Millspaugh, AMERICAN MEDICINAL PLANTS, AN ILLUSTRATED AND DESCRIPTIVE GUIDE TO THE AMERICAN PLANTS USED AS HOMEOPATHIC REMEDIES, pages 622–626 (Dover 1974); Hare et al., THE NATIONAL STANDARD DISPENSATORY, pages 766–767 (Lea Brothers 1905); Grier, *Chem. Drug. (London)* 110: 420 (1929); Grieve, A MODERN HERBAL, pages 411–415 (Hafner 1959); Stevens, *Chem. Rev.* 67: 19 (1967); Duke, CRC HANDBOOK OF MEDICINAL HERBS, page 557 (CRC Press 1985).

Pharmaceutically acceptable salts of organic acids, such as isovaleric acid, which have been approved by the U.S. Food and Drug Administration for commercial marketing include sodium, potassium, lithium, zinc, aluminum, calcium, or magnesium salts. REMINGTON'S PHARMACEUTICAL SCIENCES, 18th ed., page 1445 (Mack Publishing Co. 1990). Salts of isovaleric acid that are commercially available in the United States include the ammonium, sodium, potassium, and zinc isovalerates.

Pharmaceutically acceptable alcohols can form esters with isovaleric acid via the corresponding isovaleric acid chloride and/or anhydride by methods that are well known in the art. See, for example, March, ADVANCED ORGANIC CHEMISTRY: REACTIONS, MECHANISMS, AND STRUCTURE, fourth ed. (John Wiley and Sons 1992). Such alcohols contain one or more hydroxyl or phenol groups, and are well tolerated in vivo. Examples of suitable alcohols include ethanol, certain carbohydrates and related compounds such as glucose, fructose, sucrose, xylose, and lactose, sugar alcohols such as dulcitol, mannitol, and sorbitol, sugar acids such as gluconic and glucuronic acids, glycerol, the polyol inositol, benzyl alcohol, certain phenols such as phenol, salicylic acid, saligenin, salicylamide, vanillin, p-hydroxycinnamic acid (p-coumaric acid), caffeic acid, ferulic acid, gallic acid, ellagic acid, quercetin, and eugenol. Other examples of suitable alcohols include alkaloids and biogenic amines such as ephedrine, pseudoephedrine, phenylpropanolamine, tyramine, and dopamine, vitamins such as ascorbic acid (vitamin C), thiamine (vitamin B1), riboflavin (vitamin B2), pyridoxine (vitamin B6), cyanocobalamin (vitamin B12), the tocopherols (vitamin E), choline, folic acid, and pantothenic acid, monoterpenoid alcohols such as geraniol, nerol, and linalool, naturally occurring triterpenoid alcohols such as α- and β-amyrins, lupeol, and oleanolic and ursolic acids, bile acids such as cholic acid, deoxycholic acid, and taurocholic acid and common, naturally occurring, plant sterols (phytosterols) such as β-sitosterol, stigmasterol, campesterol, and brassicasterol. Tyler et al., PHARMACOGNOSY, 9th ed. (Lea and Febiger 1988). Other such well-tolerated hydroxyl- and phenol-containing compounds can be readily identified by those skilled in the art by consulting standard reference works such as THE MERCK INDEX and REMINGTON'S PHARMACEUTICAL SCIENCES, 18th ed. (Mack Publishing Co. 1990). Esters of isovaleric acid that are commercially available in the United States include the bornyl, ethyl, n-butyl, isoamyl, and geranyl isovalerates.

Isovaleric acid, ammonium isovalerate, and the esters ethyl isovalerate, isoamyl isovalerate, 2-methylbutyl isovalerate, cinnamyl isovalerate, methyl isovalerate, bornyl isovalerate, isobornyl isovalerate, and menthyl isovalerate, among other isovalerate esters, are listed in the Code of Federal Regulations by the FDA as being acceptable flavoring agents which may be used in foods. 21 CFR §172.515 (1991). Valerian (*Valeriana offcinalis* L.) rhizomes and roots and black haw (*Viburnum prunifolium* L.) bark are listed as acceptable natural flavoring substances and natural adjuvants in 21 CFR §172.510 (1991). Hops and "lupulin" are listed among substances that are generally recognized as safe ("GRAS"). 21 CFR §182.20 (1991).

Generally, esters of isovaleric acid are expected to be hydrolyzed in vivo by ubiquitous esterase enzymes, thereby releasing isovaleric acid and the constituent alcohol or phenol. Particularly preferred among the isovalerate esters are glyceryl mono-, di-, and especially tri-isovalerates ("triisovalerin"), isovaleryl salicylic acid or salicylate (salicylic acid isovalerate), ethyl isovalerate, and β-sitosteryl isovalerate. See FIG. 1. Hydrolysis of these isovalerate esters in vivo releases isovaleric acid and glycerol (glycerin), salicylic acid (an analgesic, anti-inflammatory, and febrifuge), ethanol (ethyl alcohol or common "alcohol," a CNS depressant), and β-sitosterol (a harmless phytosterol), respectively. With the exception of ethyl isovalerate, these esters are non-volatile or only slightly volatile, thereby minimizing any unpleasant odors. Furthermore, in pure form these esters possess the advantage of having neutral to pleasant odors, in contrast to the extremely unpleasant odors of isovaleric acid and its salts, such as the ammonium, sodium, potassium, and zinc isovalerate salts. Moreover, whereas ethyl isovalerate is a liquid, the glyceryl mono-, di-, and tri-isovalerates, isovaleryl salicylate, and β-sitosteryl isovalerate are expected to be solids at room temperature, thereby facilitating their formulation into various standard solid and liquid oral dosage forms well known in the art, such as tablets (e.g., uncoated tablets, enteric-coated tablets, and film-coated tablets), capsules, gelcaps, powders, concentrates (drops), elixirs, tinctures, and syrups.

In addition to isovaleramide, various substituted amides of isovaleric acid can be prepared by methods well known in the art. See, for example, March, ADVANCED ORGANIC CHEMISTRY: REACTIONS, MECHANISMS, AND STRUCTURE, 4th ed. (John Wiley and Sons 1992). Preferred amides for use in the present invention include N-ethyl isovaleramide, N-methyl isovaleramide, N,N-dimethyl isovaleramide, N-methyl,N-ethyl isovaleramide, N-isovaleryl GABA, N-isovaleryl glycine, and N-isovalerylglycinamide. See, for example, Tanaka et al., *J. Biol. Chem.* 242: 2966 (1967). N,N-Diethyl isovaleramide ("Valyl"), although purported to possess CNS depressant (sedative) activity, has recently been shown to possess CNS stimulant (convulsant) properties; see U.S. Pat. No. 5,506,268 and PCT application WO 94/28,888, supra. An amide of isovaleric acid with p-aminophenol also can be prepared using standard methods to provide a compound, "isovaleraminophen," which is related structurally to the drug acetaminophen (Tylenole®; see FIG. 1). In a manner analogous to that of the isovalerate esters, these substituted amides should be hydrolyzed in vivo (in this case, via hepatic amidase enzymes), releasing isovaleramide or isovaleric acid.

The compounds and preparations discussed above represent alternative forms for delivering isovaleric acid or isovaleramide in vivo. In certain cases, such as with isovaleryl salicylic acid and ethyl isovalerate, the pharmacologically active moiety corresponding to the alcohol or phenol portion may be expected to exert its own pharmacological effects. For example, compounds such as "isovaleraminophen" would be expected to exhibit a "acetaminophen-like" effect, as well as the effect expected from the isovaleric acid or isovaleramide moiety. Such novel chemical combinations of a previously known, pharmacologically active alcohol, phenol, or primary or secondary amine with isovaleric acid fall within the scope of the present invention. Similar chemical combinations with 2-methylisovaleric acid, 3-methylisovaleric acid, 2,2-dimethylisovaleric acid, 2,3-dimethylisovaleric acid, 4-methylisovaleric acid, 2,4-dimethylisovaleric acid, 3,4-dimethylisovaleric acid, 2,2,4-trimethylisovaleric acid, 3-hydroxyisovaleric acid, 4-hydroxyisovaleric acid, 4-hydroxy-3-methyl-isovaleric acid, 2-hydroxyisovaleric acid, and 2,2-dimethyl-n-butyric acid are within the scope of the present invention.

In addition to isovaleric acid, and its salts, esters and amides discussed above, the present invention also contemplates the use of compounds that are structurally related to isovaleramide. These compounds have the structure:

where A=H, CH$_3$ or OH,
  B=H, OH, or CH$_3$,
  X=CH$_2$, CHCH$_3$, C(CH$_3$)$_2$, —O—, CH(OH)—, or —CH$_2$O—,
  Y=—CO—, or —SO$_2$—, and
  Z=H, CH$_2$CO$_2$H, or CH$_2$CONH$_2$, Preferred compounds having this structure include 2-methylisovaleramide, 3-methylisovaleramide, 2,2-dimethylisovaleramide, 2,3-dimethylisovaleramide, 4-methylisovaleramide, 2,4-dimethylisovaleramide, 3,4-dimethylisovaleramide, 2,2,4-trimethylisovaleramide, 3-hydroxyisovaleramide, 4-hydroxyisovaleramide, 4-hydroxy-3-methyl-isovaleramide, 2-hydroxyisovaleramide, N-(2-acetamido)isovaleramide, 2-methyl-1-propyl sulfonamide, 1-methylethyl sulfamate, 2-methyl-1-propyl sulfamate, isopropyl carbamate, and isobutylcarbamate.

The valerian-related compounds of the present invention may be prepared using synthetic methods that are well known in the art. For example, many of the carboxylic acid precursors of the amide compounds are commercially available, for example from the Aldrich Chemical Co., Milwaukee, Wis., and can be converted into the corresponding amide by preparation of the acid chloride with thionyl chloride or oxalyl chloride, followed by reaction with ammonia or an amine. For compounds containing a hydroxyl group distal to the carboxyl group, the hydroxyl group first is protected using a suitable protecting group as described, for example, in Green, "Protective Groups in Organic Synthesis", Wiley (1981), prior to preparation of the acid chloride. 2-hydroxy and 3-hydroxy isovaleramide are metabolites of isovaleramide in vivo, and can be isolated in high yield from the urine of a patient being treated with isovaleramide.

For compounds where the starting acid is not commercially available, the required acid can be prepared by straightforward methods of organic synthesis known to the skilled chemist. For example, carboxylic acid esters may be deprotonated with a strong non-nucleophilic base, such as lithium diisopropylamide, followed by alkylation with methyl iodide or methyl trifluoromethanesulfonate. The alkylated ester is hydrolyzed and converted to the amide by the methods described above.

When the compounds contain one or more asymmetric centers, the individual enantiomers may be prepared from optically active starting materials, or separated by traditional methods of resolution, such as fractional crystallization of salts with chiral amines, or by preparation of amides with chiral amides, chromatographic separation, and hydrolysis of the amides. Alternatively, the amides can be prepared by well known methods of asymmetric synthesis, such as alkylation of an ester or amide of the acid prepared using a chiral auxiliary. See, for example, Evans et al, *Tetrahedron*, 44:5525 (1988) and Fadel et al. *Asymmetry* 1994:531.

The NSAID compounds suitable for use in the present invention are well known in the art. NSAID compounds generally may be divided into sub-classes based upon their structural type, as shown below:

| Sub-class | Examples |
|---|---|
| Acetylsalicylic acid | aspirin |
| acetic acids | diclofenac |
|  | indomethacin |
|  | ketorolac |
|  | nabumetone |
|  | sulindac |
|  | tolmetin |
| fenamates | meclofenamate |
|  | mefenamic acid |
| oxicams | piroxicam |
| propionic acids | ibuprofen |
|  | ketoprofen |
|  | naproxen |
|  | oxaprozin |

Each of these classes of compounds is suitable for use in the present inventions. NSAID compounds that may be used in combination with valerian extracts and/or with the valerian related compounds described above include those described in Chapter 27 of GOODMAN AND GILMAN'S THE PHARMACOLOGICAL BASIS OF THERAPEUTICS, 9th ed., pages 617–657 (McGraw-Hill, 1996), which is hereby incorporated by reference in its entirety.

These compounds include, but are not limited to salicylates, including aspirin, sodium salicylate, acetaminophen, phenacetin, ibuprofen, ketoprofen, indomethacin, flurbiprofen, diclofenac, naproxen, piroxicam, tebufelone, etodolac, nabumetone, tenidap, alcofenac, antipyrine, amimopyrine, dipyrone, anirnopyrone, phenylbutazone, clofezone, oxyphenbutazone, prexazone, apazone, benzydanine, bucolome, cinchopen, clonixin, ditrazol, epirizole, fenoprofen, floctafeninl, flufenamic acid, glaphenine, indoprofen, meclofenamic acid, mefenamic acid, niflumic acid, salidifamides, sulindac, suprofen, tolmetin, nabumetone, tiaramide, proquazone, bufexamac, flumizole, tinoridine, timegadine, dapsone, diflunisal, benorylate, fosfosal, fenclofenac, etodolac, fentiazac, tilomisole, carprofen, fenbufen, oxaprozin, tiaprofenic acid, pirprofen, feprazone, piroxicam, sudoxicam, isoxicam, celecoxib, Vioxx® and tenoxicam. Each of these compounds is commercially available or may be prepared by methods that are well known in the art.

Preparation of Pharmaceutical Compositions

The present invention also is directed to pharmaceutical compositions containing combinations of the active compounds described above. The pharmaceutical compositions can contain combinations of two or more of the active compounds. The pharmaceutical formulations of the present invention can be prepared according to known methods, whereby active agents are combined in a mixture with a pharmaceutically acceptable carrier. For instance, see REMINGTON'S PHARMACEUTICAL SCIENCES and GOODMAN AND GILMAN'S, both cited above. A composition is said to be in a "pharmaceutically acceptable carrier" if its administration can be tolerated by a recipient patient. Sterile phosphate-buffered saline is one example of a pharmaceutically acceptable carrier. Other suitable carriers (e.g. saline and Ringer's solutions) are well known to those skilled in the art. See, for example, REMINGTON'S PHARMACEUTICAL SCIENCES, supra.

In general, the dosages of the muscle-tone decreasing agents and the NSAID compounds described herein will vary depending upon such factors as the patient's age, weight, height, sex, general medical condition, and previous medical history. For purposes of therapy, a compound of the present invention and a pharmaceutically acceptable carrier are administered to a subject in need of such treatment in a therapeutically effective amount. The combination of active agent and carrier is said to be administered in a "therapeutically effective amount" if the amount administered is physiologically significant. An agent is physiologically significant if its presence results in a detectable change in the physiology of a recipient patient. In the present context, for example, a muscle tone-decreasing agent is physiologically significant if the presence of the agent results in the alleviation of muscle pain.

Isovaleramide and structurally-compounds can be administered orally using solid oral dosage forms such as enteric-coated tablets, caplets, gelcaps, or capsules, or via liquid oral dosage forms such as syrups or elixirs. The indicated dosage of isovaleramide and related compounds as agents that elicit reductions in muscle tone and pain is on the order of 50–1200 mg per dose. Unit solid oral dosage forms preferably contain about 200–600 mg of active ingredient per tablet or capsule, at a dosage of 1–20 mg/kg body weight. Liquid formulations can also be employed with active ingredient compositions so as to provide 1–2 teaspoonfuls per dose. Furthermore, corresponding reduced dosage pediatric chewable and liquid oral dosage forms can also be prepared and administered. These compounds also can be added to foods and beverages in the form of drops (with a dropper from a "concentrate" preparation) for oral administration. In addition, compounds such as isovaleramide may be formulated into chewing gum to facilitate oral delivery and absorption. Appropriate dosages for each of the NSAID compounds used in the present invention are well known in the art.

Alternatively, isovaleramide and related compounds can be administered by injection or other systemic routes, such as transdermal or transmucosal administration, for example, nasally, buccally, or rectally, via suppositories. Oral administration is much more convenient, however, and therefore is preferred.

The present invention thus contemplates a variety of pharmaceutical compositions containing isovaleramide, isovaleric acid, and/or its pharmaceutically acceptable salts, substituted amides, and alcohol esters as active ingredients that are suitable for oral, parenteral, transdermal, transmucosal, intranasal, buccal, or rectal administration. Although such compounds may be present as incidental by-products in certain pharmaceutical formulations which are outside the scope of the present invention, the common feature of the present formulations is that isovaleramide, isovaleric acid, and/or its pharmaceutically acceptable salts, substituted amides, and alcohol esters are present in a standardized amount. That is, the pharmaceutical formulations contain a predetermined, chemically defined, and quantifiable amount of at least one of such compounds to enable the determination of the quantity of a particular composition required to achieve the dosage levels described herein.

It is further understood that isovaleramide and/or related compounds can be used in combination with other pharmaceutically active ingredients, such as NSAIDs to prepare novel pharmaceutical compositions.

3. DEMONSTRATING THERAPEUTICALLY-RELEVANT ACTIVITY

The suitability and effectiveness of a given pharmaceutical formulation for the alleviation of a pathology, as discussed above, can be demonstrated using case studies such as (but not limited to) those described below.

A commercially prepared extract of valerian (Baldriparan stark N, a preparation from Germany, containing alcohol/water extracts of Baldrian (valerian) Hopfen (hops), and Melissa (lemon balm) in a coated hard-pressed tablet was taken in combination with ibuprofen to obtain improved, greater relief from lower back pain due to undue stress/exercise than the relief that can be obtained with either preparation administered by itself.

Set forth below are two individual case reports from persons using the above combination for relief of pain and muscle tension resulting from injury to the lower back due to exercise or stress. These examples are provided for purposes of illustration and are not intended to be limiting of the invention.

EXAMPLE 1

Use of a Valerian Preparation and Ibuprofen to Alleviate Pain and Increased Muscle Tone Due to Recurrent, Excessive Lower Back Pain.

A male, age 33 years, was complaining of recurrent excessive lower back pain from prior injuries. During a bout of lower back pain, he stated that he could not sleep or sit comfortably and was in duress from the constant pain. He had tried using Doan's Pills and various amounts of ibuprofen, aspirin, or acetaminophen without any useful sense of relief. Likewise, he had tried two of the Baldriparan tablets without any useful sense of relief. It was suggested that he try taking two of the Baldriparan tablets along with 400 mg of ibuprofen. It was stated that the ibuprofen would provide a decrease in inflammation and some analgesic therapy whereas the addition of the valerian and hops extract could provide a decrease in the muscle tone and analgesia as well, thereby allowing for relief from the pain. The next morning, he reported that he took the novel combination of Baldriparan and ibuprofen as suggested before he went to bed. Not only did he sleep well, but he also reported considerable relief from the pain of his back upon awakening. His spouse stated that he "acted like a new man" because he was not grimacing and stooped from pain. He continued to take this combination over the next several days and it continued to provide exceptional relief, without any adverse side effects such as cognition impairment, sedation or withdrawal symptoms.

EXAMPLE 2

Use of a Valerian Preparation and Ibuprofen to Alleviate Pain and Increased Muscle Tone Due to an Acute Muscle Strain from Overexertion A female, age 23 years, complained of excessive lower back pain that interfered with sleeping and the general activities of daily living such as sitting or standing. She had injured her back while shoveling deep snow from her driveway and sidewalk. She had been taking ibuprofen but experiencing little relief. It was suggested that she take two tablets of the valerian preparation (as stated in the above example) with 400 mg of ibuprofen for the same reasons stated in the first example. The next day she reported that she experienced significant relief from the pain and requested additional tablets. She also stated that she did not experience any adverse effects from the preparation. She continued to take the combination until her back healed and no longer gave her pain without medication.

What is claimed is:

1. The use of a combination of: (a) at least one non-steroidal anti-inflammatory compound, and; (b) at least one compound selected from the group consisting of isovaleric acid, a pharmaceutically acceptable salt of isovaleric acid, a pharmaceutically acceptable ester of isovaleric acid, a pharmaceutically acceptable amide of isovaleric acid and a compound having the structure:

wherein A=H, $CH_3$ or OH,
  B=H, OH, or $CH_3$,
  X=$CH_2$, $CHCH_3$, $C(CH_3)_2$, —O—, $CH(OH)$—, or —$CH_{20}$—,
  Y=—CO—, or —$SO_2$—, and
  Z=H, $CH_2CO_2H$, or $CH_2CONH_2$
and wherein said compound is selected from the group consisting of 2-methyl isovaleramide, 3-methylisovaleramide, 2,2-dimethylisovaleramide, 2,3-dimethylisovaleramide, 4methylisovaleramide, 2,4-dimethylisovaleramide, 3,4-dimethylisovaleramide, 2,2,4-trimethylisovaleramide, 3-hydroxyisovaleramide, 4-hydroxyisovaleramide, 4-hydroxy-3-methyl-isovaleramide, 2-hydroxyisovaleramide, N-(2-acetamido) isovaleramide, 2-methyl-1-propyl sulfonamide, 1-methylethyl sulfamate, 2-methyl-1-propyl sulfamate, isopropyl carbamate, and isobutylcarbamate,
  in the preparation of a pharmaceutical formulation for use in a method of treating a pathology that is ameliorated by a decrease in muscle tone and a reduction in inflammation, whereby at least one symptom of said pathology is alleviated.

2. A use according to claim 1, wherein said pathology is selected from the group consisting of acute muscular aches, strains, and sprains which occur from a localized, external insult to a particular muscle or muscle group outside of, or peripheral to, the CNS.

3. A use according to claim 2, wherein said pathology is lower back pain.

4. A use according to claim 1, wherein said pathology is ameliorated by a decrease in inflammation, pain, and muscle tone.

5. A use according to claim 1, wherein said non-steroidal anti-inflammatory compound is selected from the group consisting of aspirin, a non-steroidal anti-inflammatory acetic acid, a fenamate, an oxicam, and a non-steroidal anti-inflammatory propionic acid.

6. A use according to claim 1, wherein said non-steroidal anti-inflammatory compound is selected from the group consisting of sodium salicylate, acetaminophen, phenacetin, ibuprofen, ketoprofen, indomethacin, flurbiprofen, diclofenac, naproxen, piroxicam, tebufelone, etodolac, nabumetone, tenidap, alcofenac, antipyrine, amimopyrine, dipyrone, animopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, meclofenamic acid, mefenamic acid, niflumic acid, salidifamides, sulindac, suprofen, tolmetin, nabumetone, tiaramide, proquazone, bufexamac, flumizole, tinoridine, timegadine, dapsone, diflunisal, benorylate, fosfosal, fenclofenac, etodolac, fentiazac, tilomisole, carprofen, fenbufen, oxaprozin, tiaprofenic acid, pirprofen, feprazone, piroxicam, sudoxicam, isoxicam, celecoxib, Vioxx® and tenoxicam.

7. A use according to claim 6, wherein said non-steroidal anti-inflammatory compound is selected from the group consisting of aspirin, sodium salicylate, acetaminophen, ibuprofen, ketoprofen, and naproxen.

8. A use according to claim 1, wherein said composition comprises a pharmaceutically acceptable amide of isovaleric acid, and wherein said amide is isovaleramide.

9. A use according to claim 8, wherein said composition comprises isovaleramide and ibuprofen.

10. A use according to claim 8, wherein said composition comprises isovaleramide and aspirin.

11. A use according to claim 8, wherein said composition comprises isovaleramide and acetaminophen.

12. A use according to claim 8, wherein said composition comprises isovaleramide and acetylsalicylic acid.

13. A use according to claim 8, wherein said composition comprises isovaleramide and naproxen.

14. A use according to claim 8, wherein said composition comprises isovaleramide and ketoprofen.

15. Use of an extract of Valerianaceae, cramp bark, black haw, or hops in combination with at least one non-steroidal anti-inflammatory compound in the preparation of a pharmaceutical formulation for use in a method of treating acute muscular aches, strains, and sprains which occur from a localized, external insult to a particular muscle or muscle group outside of, or peripheral to, the CNS wherein said extract comprises at least one compound that is hydrolyzed in vivo to yield isovaleric acid or isovaleramide.

16. A use according to claim 15, wherein said non-steroidal anti-inflammatory compound is ibuprofen.

17. A use according to claim 15, wherein said non-steroidal anti-inflammatory compound is aspirin.

18. A use according to claim 15, wherein said non-steroidal anti-inflammatory compound is acetaminophen.

19. A use according to claim 15, wherein said non-steroidal anti-inflammatory compound is acetylsalicylic acid.

20. A use according to claim 15, wherein said non-steroidal anti-inflammatory compound is naproxen.

21. A use according to claim 15, wherein said non-steroidal anti-inflammatory compound is ketoprofen.

22. A pharmaceutical composition comprising (a) at least one non-steroidal anti-inflammatory compound, and; (b) at least one compound selected from the group consisting of isovaleric acid, a pharmaceutically acceptable salt of isovaleric acid, a pharmaceutically acceptable ester of isovaleric acid, a pharmaceutically acceptable amide of isovaleric acid and a compound having the structure:

wherein A=H, CH$_3$ or OH,
B=H, OH, or CH$_3$,
X=CH$_2$, CHCH$_3$, C(CH$_3$)$_2$, —O—, CH(OH)—, or —CH$_2$O—,
Y=—CO—, or —SO$_2$—, and
Z=H, CH$_2$CO$_2$H, or CH$_2$CONH$_2$
and wherein said compound is selected from the group consisting of 2-methyl isovaleramide, 3-methylisovaleramide, 2,2-dimethylisovaleramide, 2,3-dimethylisovaleramide, 4-methylisovaleramide, 2,4-dimethylisovaleramide, 3,4-dimethylisovaleramide, 2,2,4-trimethylisovaleramide, 3-hydroxyisovaleramide, 4-hydroxyisovaleramide, 4-hydroxy-3-methylisovaleramide, 2-hydroxyisovaleramide, N-(2-acetamido) isovaleramide, 2-methyl-1-propyl sulfonamide, 1-methylethyl sulfamate, 2-methyl-1-propyl sulfamate, isopropyl carbamate, and isobutylcarbamate,
together with a pharmaceutically acceptable diluent, excipient, or carrier.

23. A composition according to claim 22, wherein said non-steroidal anti-inflammatory compound is selected from the group consisting of aspirin, a non-steroidal antiinflammatory acetic acid, a fenamate, an oxicam, and a non-steroidal anti-inflammatory propionic acid.

24. A composition according to claim 22 wherein said non-steroidal anti-inflammatory compound is selected from the group consisting of sodium salicylate, acetaminophen, phenacetin, ibuprofen, ketoprofen, indomethacin, flurbiprofen, diclofenac, naproxen, piroxicam, tebufelone, etodolac, nabumetone, tenidap, alcofenac, antipyrine, amimopyrine, dipyrone, animopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, meclofenamic acid, mefenamic acid, niflumic acid, salidifamides, sulindac, suprofen, tolmetin, nabumetone, tiaramide, proquazone, bufexamac, flumizole, tinoridine, timegadine, dapsone, diflunisal, benorylate, fosfosal, fenclofenac, etodolac, fentiazac, tilomisole, carprofen, fenbufen, oxaprozin, tiaprofenic acid, pirprofen, feprazone, piroxicam, sudoxicam, isoxicam, celecoxib, Vioxx® and tenoxicam.

25. A composition according to claim 22, wherein said non-steroidal anti-inflammatory compound is selected from the group consisting of aspirin, sodium salicylate, acetaminophen, ibuprofen, ketoprofen, and naproxen.

26. A composition according to claim 22, wherein said composition comprises a pharmaceutically acceptable amide of isovaleric acid, and wherein said amide is isovaleramide.

27. A composition according to claim 22, wherein said composition comprises isovaleramide and ibuprofen.

28. A composition according to claim 22, wherein said composition comprises isovaleramide and aspirin.

29. A composition according to claim 22, wherein said composition comprises isovaleramide and acetaminophen.

30. A composition according to claim 22, wherein said composition comprises isovaleramide and acetylsalicylic acid.

31. A composition according to claim 22, wherein said composition comprises isovaleramide and naproxen.

32. A composition according to claim 22, wherein said composition comprises isovaleramide and ketoprofen.

33. A pharmaceutical composition comprising an extract of Valerianaceae, cramp bark, black haw, or hops and at least one non-steroidal anti-inflammatory compound, together with a pharmaceutically acceptable diluent, excipient, or carrier.

34. A composition according to claim 33, wherein said non-steroidal anti-inflammatory compound is ibuprofen.

35. A composition according to claim 33, wherein said non-steroidal anti-inflammatory compound is aspirin.

36. A composition according to claim 33, wherein said non-steroidal anti-inflammatory compound is acetaminophen.

37. A composition according to claim 33, wherein said non-steroidal anti-inflammatory compound is acetylsalicylic acid.

38. A composition according to claim 33, wherein said non-steroidal anti-inflammatory compound is naproxen.

39. A composition according to claim 33, wherein said non-steroidal anti-inflammatory compound is ketoprofen.

* * * * *